United States Patent
Moore

(10) Patent No.: US 8,053,020 B2
(45) Date of Patent: Nov. 8, 2011

(54) PROCESS FOR COATING A PORTION OF AN IMPLANTABLE MEDICAL DEVICE

(75) Inventor: William F. Moore, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 479 days.

(21) Appl. No.: 12/393,213

(22) Filed: Feb. 26, 2009

(65) Prior Publication Data

US 2009/0226599 A1  Sep. 10, 2009

Related U.S. Application Data

(60) Provisional application No. 61/032,249, filed on Feb. 28, 2008.

(51) Int. Cl.
*A61L 27/02* (2006.01)
(52) U.S. Cl. .............. 427/2.25; 427/2.24; 427/2.28
(58) Field of Classification Search ............ 427/2.24, 427/2.25, 2.28
See application file for complete search history.

(56) References Cited

U.S. PATENT DOCUMENTS

| | | | |
|---|---|---|---|
| 4,781,719 A | 11/1988 | Kelman | |
| 5,271,233 A | 12/1993 | Parker et al. | |
| 5,624,704 A | 4/1997 | Darouiche et al. | |
| 6,568,235 B1 | 5/2003 | Kokish | |
| 7,070,832 B2 | 7/2006 | Goldstein | |
| 7,198,675 B2 | 4/2007 | Fox et al. | |
| 2002/0115559 A1 | 8/2002 | Batchelor et al. | |
| 2004/0098106 A1 | 5/2004 | Williams et al. | |
| 2004/0213893 A1 | 10/2004 | Boulais | |
| 2004/0224868 A1 | 11/2004 | Meyerhoff et al. | |
| 2005/0165472 A1* | 7/2005 | Glocker | 623/1.15 |
| 2006/0147492 A1* | 7/2006 | Hunter et al. | 424/426 |
| 2006/0213077 A1* | 9/2006 | Tanaka et al. | 34/423 |
| 2007/0043431 A1 | 2/2007 | Melsheimer | |
| 2007/0063365 A1 | 3/2007 | Giacobbe et al. | |
| 2007/0074539 A1 | 4/2007 | Rossewey | |
| 2007/0141232 A1 | 6/2007 | Tochterman et al. | |
| 2009/0309273 A1* | 12/2009 | Parker | 264/573 |

FOREIGN PATENT DOCUMENTS

| | | |
|---|---|---|
| JP | 63-080942 | 4/1988 |
| WO | 03/006180 | 1/2003 |

OTHER PUBLICATIONS

English Abstract of JP S63-080942.

* cited by examiner

*Primary Examiner* — John Hardee
(74) *Attorney, Agent, or Firm* — Brinks Hofer Gilson & Lione

(57) ABSTRACT

Methods are provided for coating a first surface of a device while also preventing coating of a second surface of the device by forming a covering of solid carbon dioxide on the second surface. In one embodiment of the invention, a method is provided for coating a luminal surface of a device while masking the abluminal surface with a covering of solid carbon dioxide. In another embodiment, a method is provided for coating the abluminal surface of the device while covering the luminal surface of the device with solid carbon dioxide.

20 Claims, 3 Drawing Sheets

PROCESS FOR COATING A PORTION OF AN IMPLANTABLE MEDICAL DEVICE

This application claims priority to U.S. Provisional Application No. 61/032,249, filed Feb. 28, 2008, which is hereby incorporated by reference.

TECHNICAL FIELD

The present invention relates to methods of coating medical devices, such as open-celled endovascular and coronary stents.

BACKGROUND

It has become common to treat a variety of medical conditions by introducing an implantable medical device partly or completely into the esophagus, trachea, colon, biliary tract, urinary tract, vascular system or other location within a human or veterinary patient. For example, many treatments of the vascular system entail the introduction of a device such as a stent, a catheter, a balloon, a wire guide, a cannula, or the like.

For certain applications, the medical device is coated with a therapeutic agent adapted to expose tissue within the body to the therapeutic agent. For many treatments, it may be desirable to employ a medical device having therapeutic agents only on one surface. Alternatively, it may be desirable to employ a medical device having different therapeutic agents on the various surfaces of the device.

For certain medical applications, a coating containing a therapeutic agent is applied to the external surface of a medical device. The medical device may be configured to bring the coating into therapeutically effective contact with the wall of a body vessel. For instance the medical device may be a radially expandable tubular stent formed by a plurality of interconnected members defining open cells extending between an external (abluminal) surface and an internal (luminal) surface. A releasable therapeutic agent may be applied to the abluminal surface of the stent for delivery to a treatment site within a body vessel. The luminal surface defines a tubular lumen extending axially from the proximal end to the distal end of the stent. Such coated stent structures are commonly deployed within a body vessel to maintain patency of a stenosis, and the therapeutic agent may be selected to mitigate or prevent restenosis of the body vessel after dilation.

Coatings have been applied to medical devices by processes such as dipping, spraying, vapor deposition, plasma polymerization, and electrodeposition. Although these processes have been used to produce satisfactory coatings, they have numerous, associated potential drawbacks. For example, it may be difficult to achieve coatings of uniform thicknesses, both on individual parts and on batches of parts. Furthermore, coating material may collect around contact points between the device and the supporting apparatus, which is referred to "webbing" of the coating. When the supporting apparatus is removed from the device, the webbed material may stick to the supporting apparatus, thereby removing some of the needed coating from the device and leaving bare areas. The webbed material may also stick to the device. In addition, coating material may collect or bridge between openings of cellular devices. Upon implantation and expansion of the device, this webbed and/or bridged material may dislodge and then fall through openings in the device. Additionally, these coating processes may require that the coated part be held during coating, which may result in defects such as bare spots where the part was held and which may thus require subsequent coating steps. Furthermore, many conventional processes require multiple coating steps or stages for the application of a second coating material, or to allow for drying between coating steps or after the final coating step.

SUMMARY

Methods of coating a portion of a device having at least a first surface and a second surface are provided. The methods include the steps of applying a mask to the first surface of the device, forming a covering of solid carbon dioxide on the second surface of the device, removing the mask from the first surface, applying a coating to the first surface, and then removing the covering of solid carbon dioxide from the second surface. In one embodiment, the solid carbon dioxide will sublimate thereby eliminating or reducing the tearing of the coating, as opposed to shielding the second surface with a mandrel that must be forcibly removed and may damage the coating.

In one embodiment, the method includes the steps of masking the first surface of the device by placing the device into a cavity formed in a masking body, forming a plug of solid carbon dioxide in the cavity so that the plug covers the second surface of the device, removing the device and the plug of solid carbon dioxide from the cavity, and then applying a coating to the first surface of the device.

In another embodiment, the method includes the steps of placing a stent onto a mandrel so that the mandrel masks the luminal surface, placing the mandrel and the stent into a cavity formed in a masking body, forming a plug of solid carbon dioxide in a space formed between the stent and mandrel and a wall of the cavity so that the plug of solid carbon dioxide covers the abluminal surface of the device, removing the mandrel from the stent and the plug of solid carbon dioxide, and applying a coating to at least a portion of the luminal surface of the stent.

In another embodiment, the method includes the steps of placing the stent into a cavity formed in an elastomeric masking body so that the cavity masks the abluminal surface of the stent, placing a mandrel in the center of the cavity and the stent so that the cavity, stent, and mandrel are approximately concentrically spaced, forming a plug of solid carbon dioxide in the cavity of the masking body so that the plug covers the luminal surface of the stent, removing the stent and the plug of solid carbon dioxide from the cavity in the masking body, applying a coating to the abluminal surface of the stent, and warming the stent and the solid plug of carbon dioxide to cause the solid carbon dioxide to sublimate.

DESCRIPTION OF THE ILLUSTRATIVE EMBODIMENTS

Figure 1:
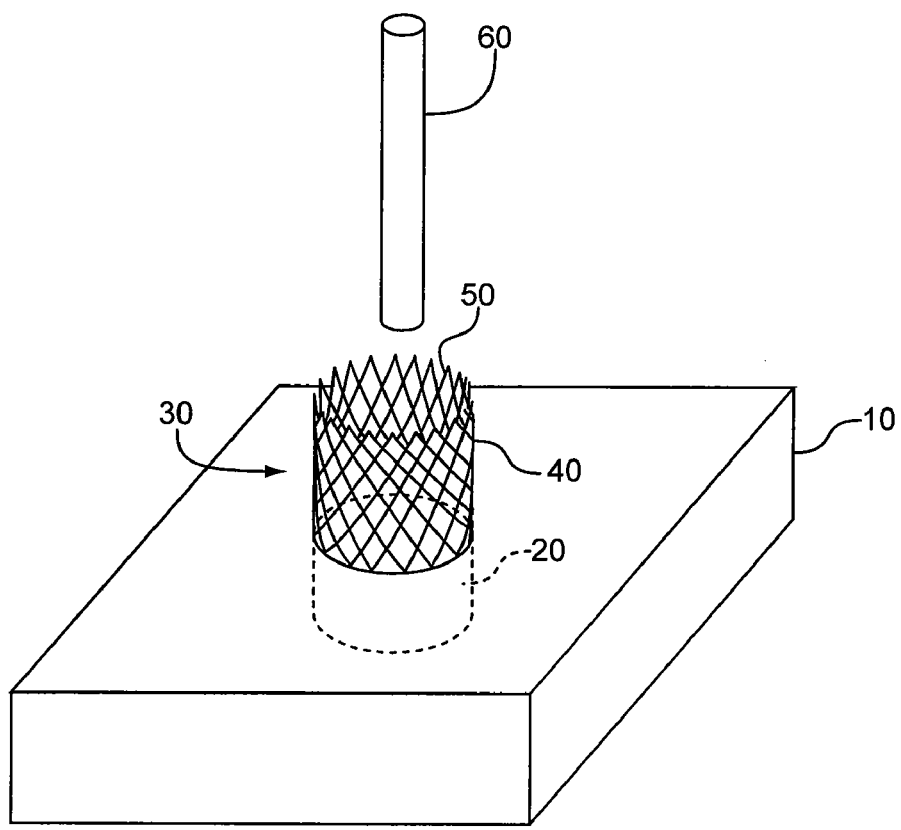
FIG. 1 is a depiction of one embodiment of a coating-process showing a stent and mandrel being placed into the cavity of a masking body prior to formation of the solid carbon dioxide covering.

The present disclosure relates to methods of coating a medical device. For the purposes of promoting an understanding of the principles of the invention, reference will now be made to the embodiments illustrated in the drawings, and specific language will be used to describe the same. It should be understood that no limitation of the scope of the invention is intended, and that reference to specific embodiments, materials, and methods are made only for illustrative purposes.

Definitions

As used herein, the term "therapeutic agent" refers to any pharmaceutically active agent that results in an intended therapeutic effect on the body to treat or prevent conditions or diseases.

The term "biodegradable" refers to materials selected to dissipate upon implantation within a body, independent of which mechanisms by which dissipation can occur, such as dissolution, degradation, absorption and excretion. The actual choice of which type of materials to use may readily be made by one of ordinary skill in the art. Such materials are often referred to by different terms in the art, such as "bioresorbable," "bioabsorbable," or "biodegradable," depending upon the mechanism by which the material dissipates. The prefix "bio" indicates that the erosion occurs under physiological conditions, as opposed to other erosion processes, caused for example, by high temperature, strong acids or bases, UV light or weather conditions.

A "biocompatible" material is a material that is compatible with living tissue or a living system by not being toxic or injurious and not causing immunological rejection.

A "non-bioabsorbable" or "biostable" material refers to a material, such as a polymer or copolymer, which remains in the body without substantial bioabsorption.

The term "spray methods" refers to a method of applying a material using a pressurized spray of material from a jet or nozzle.

The term "abluminal" refers to the exterior surface of a generally tubular device.

The term "luminal" refers to the interior surface of a generally tubular device.

Exemplary Descriptions of the Coating Method

Figure 2:
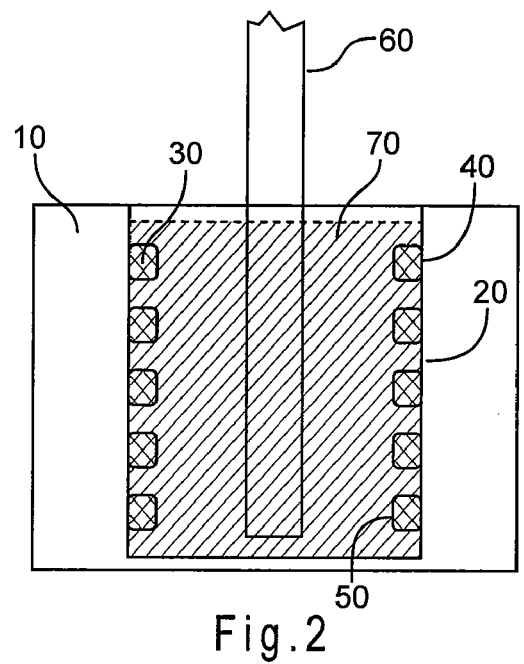
FIG. 2 is a cross-sectional view of the masking body, stent, and mandrel, showing the void between the mandrel and the stent luminal surface in which solid carbon dioxide is to be formed.
Figure 3:
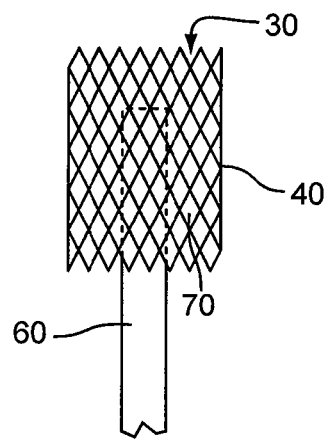
FIG. 3 is a depiction of an embodiment showing a stent having the solid carbon dioxide covering formed between the stent's luminal surface and a mandrel body.

In a first embodiment shown in FIGS. 1-3, a masking body (10) includes a cavity (20). The cavity (20) is dimensioned so that a surface to be coated fits against the masking body so that solid carbon dioxide does not cover that surface. In one embodiment, the masking body may be made from an elastomeric material, for example from silicone or polyethylene. In the embodiment shown in FIGS. 1-3, the device to be coated comprises a radially deformable stent (30), which has an abluminal surface (40) and a luminal surface (50).

As shown in FIG. 1, the stent (30) is placed into the cavity (20) such that the wall of the cavity and the abluminal surface (40) fit together tightly. To achieve such a fit, the stent (30) is compressed in its radial direction and then placed into the cavity (20), wherein it expands to form a tight fit. Thereafter, a mandrel (60) is placed into the cavity so that it does not touch the luminal surface (50) or the cavity (20). As depicted in FIG. 2, solid carbon dioxide is then formed filling the cavity (20) and the space between the luminal surface (50) and the mandrel (60) to create a solid carbon dioxide plug (70). The stent (30), solid carbon dioxide plug (70), and the mandrel (60) are then removed from the masking body (10). Once removed from the masking body (10), the abluminal surface (40) is exposed and ready for coating application.

FIG. 3 shows the stent (30), solid carbon dioxide plug (70), and mandrel (60) after removal from the masking body (10). The mandrel (60) provides a surface to grip or clamp into place. At this point, coating materials may be applied to the abluminal surface (40). In one embodiment, the coatings are applied using a spray method, such as ultrasonic spray deposition. However, coatings may be applied by other methods known to those skilled in the relevant art. It should be understood that one coating or multiple layers of coatings may be applied to the abluminal surface. After forming the solid carbon dioxide plug (70), the stent (30) and solid carbon dioxide plug (70) should be kept below around or below the sublimation temperature of the solid carbon dioxide until the coatings have been applied.

After the coatings are applied to the device, the device and carbon dioxide are warmed to cause the solid carbon dioxide to sublime. This advantageously eliminates or reduces tearing of the coating material, because there is no need to forcibly remove a mandrel from the coated device. In one embodiment, after applying coatings to the device, the stent (30) and the solid carbon dioxide plug (70) are placed into a warmed vacuum chamber and the pressure is reduced. This helps reduce or avoid webbing and bridging because material attached to the solid carbon dioxide plug (70) may be removed by the vacuum as the carbon dioxide sublimes.

Figure 4:
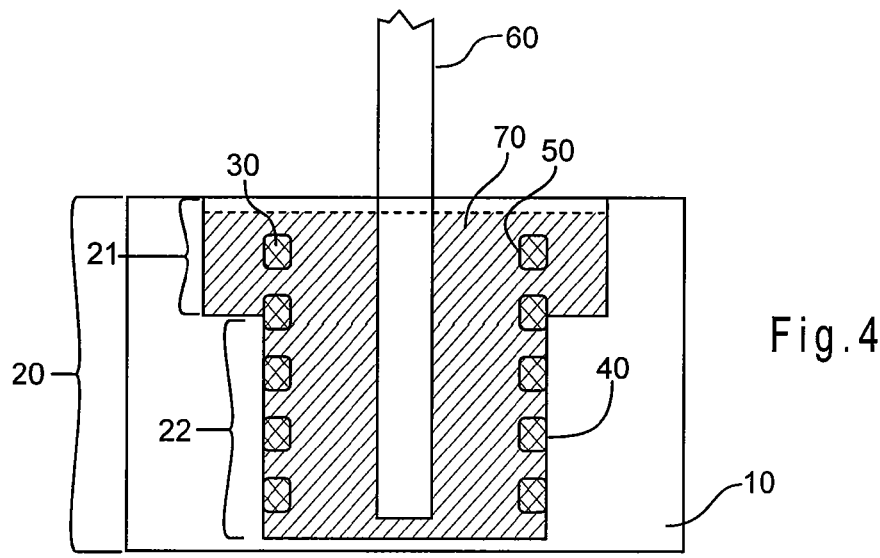
FIG. 4 is a cross-sectional depiction of an embodiment in which only a portion of the abluminal surface of the device is coated.

FIG. 4 is an illustration of an alternate embodiment of the method. In this embodiment, the masking body (10) is configured so that only a portion of the abluminal surface (40) will be exposed to coating materials. The masking body (10) in this embodiment has a cavity (20) having a portion with a larger dimension (21) and a smaller dimension (22). The smaller dimension portion (22) corresponds in size to the dimension of the device (30) or is slightly smaller. Thus, the smaller dimension portion (22) forms a tight fit with the abluminal surface (40). When formed, the solid carbon dioxide plug covers the luminal surface (50) of the device that corresponds to the smaller dimension portion of the cavity (22) as well as a portion of the abluminal surface (40) that corresponds to the larger dimension portion of the cavity (21). Upon removal of the masking body (10), only the portion of the abluminal surface corresponding to the smaller dimension (22) portion of the cavity is exposed for coating application.

Figure 5:
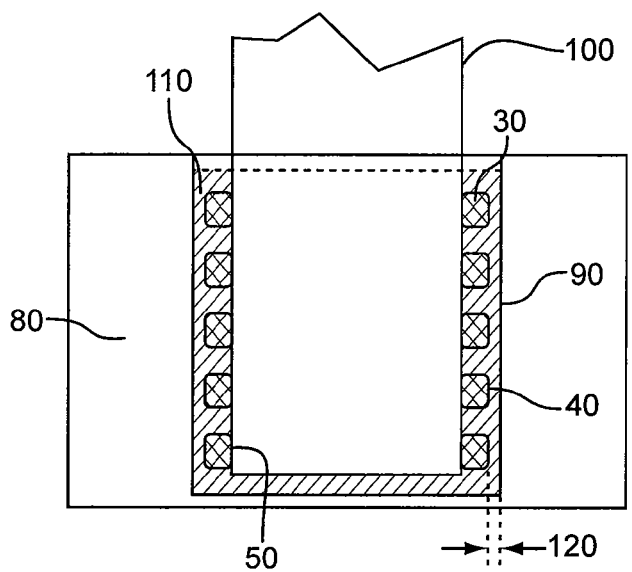
FIG. 5 is a cross-sectional depiction of an embodiment showing a stent mounted on a mandrel to mask the stent's luminal surface. This combination is placed into an opening in a body into which solid carbon dioxide is formed.
Figure 6:
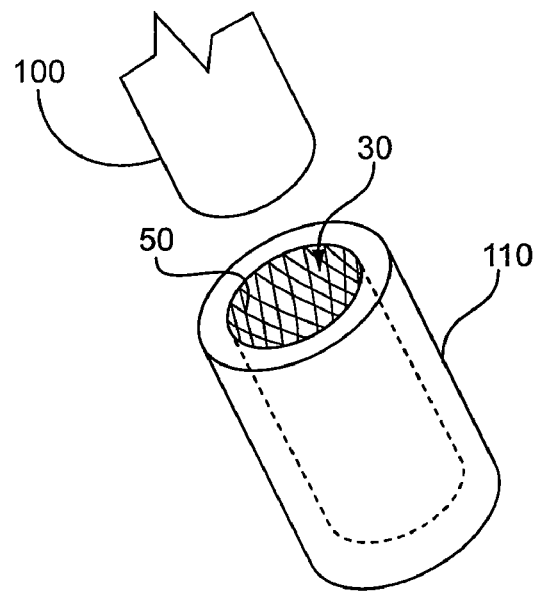
FIG. 6 is a depiction of an embodiment in which a stent, having received a covering of solid carbon dioxide, is removed from the body and the mandrel has been removed to expose the luminal portion for coating.

FIGS. 5 and 6 illustrate another alternate embodiment of the method disclosed herein. FIG. 5 illustrates a cross-sectional view of this alternate embodiment, which provides a method of coating the luminal portion of the device. The embodiment involves placing the device (30), for example a stent, on a mandrel (100) that forms a snug fit with the luminal surface (50) of the device. The mandrel (100) may be made from an elastomeric material, for example from silicone or polyethylene. Those skilled in the art understand that the mandrel may be made from other materials as well. The mandrel (100) and the stent (30) are then inserted into a cavity

(90) in a masking body (80). In this embodiment, the cavity (90) is sufficiently larger than the outside dimension of the device (30) so that a space (120) is present between the abluminal surface (40) and the wall of the cavity (90). A plug of solid carbon dioxide (110) is then formed in the space (120) between the abluminal surface (40) and the cavity (90).

Once the solid carbon dioxide plug (110) is formed, the mandrel (100) is removed from the stent (30) and solid carbon dioxide plug (110) to expose the luminal surface (50). The masking body (80) may also be removed as shown in FIG. 6, or alternatively the masking body (80) may be left in place and used to grip or clamp the stent (30) during coating application. In one embodiment, the coating is applied using a spray method, such as ultrasonic spray deposition. However, coatings may be applied by other methods known to those skilled in the art for example by dipping the device into a coating solution. During the coating process, the stent (30) and solid carbon dioxide plug (110) are kept around or below the sublimation temperature of the solid carbon dioxide.

After applying the coatings, the device is warmed to remove the carbon dioxide. In one embodiment, this is done in a vacuum chamber with the pressure reduced. The advantages associated with these embodiments are similar to those described above in conjunction with the embodiments shown in FIGS. 1-3.

Figure 7:
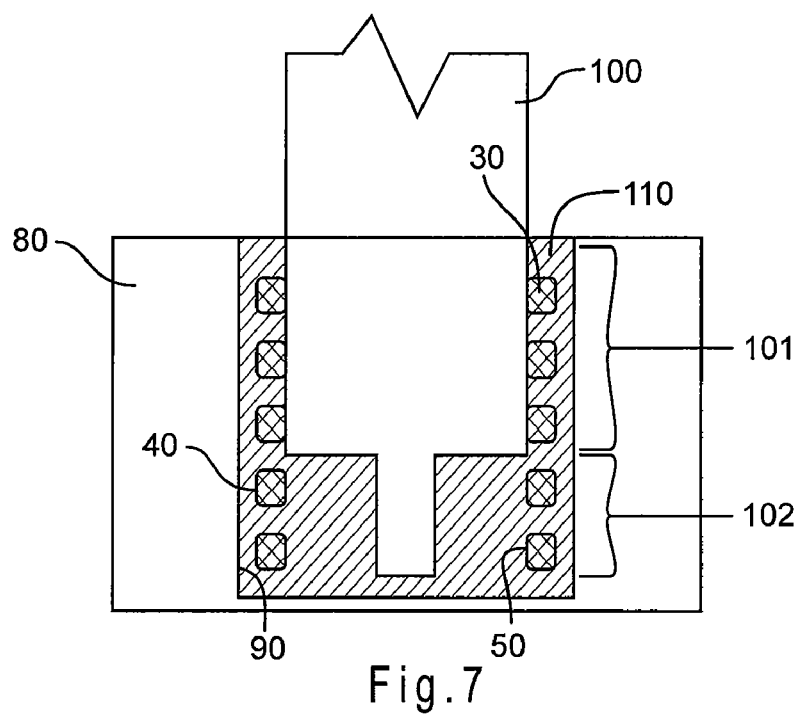
FIG. 7 is a depiction of an embodiment in which only a portion of the luminal surface of a device is prepared for coating.

In another embodiment of the method, shown in FIG. 7, a portion of the luminal surface (50) is coated. In this embodiment, a mandrel (100) has a first portion with a smaller dimension (102) and a second portion (101) dimensioned to form a tight fit with the device. The mandrel (100) and the device (30) are then placed in a cavity (90) of a masking body (80). The solid carbon dioxide plug (110) is formed around the abluminal surface (40) of the device corresponding to the larger dimension portion of the mandrel (101) and both the abluminal surface (40) and luminal surface (50) portions of the device (30) corresponding to the smaller dimension portion of the mandrel (102). Thus, after the mandrel is removed, the portion of the luminal surface (50) corresponding to the larger dimension portion (101) is free from solid carbon dioxide and exposed for coating application.

It should be understood that any of the embodiments described above may be combined. For example, one coating material may be applied to the abluminal surface while another coating is applied to the luminal surface. Additionally, the coatings may comprise layers of different materials. For example, a coating layer containing a therapeutic agent may be applied and thereafter a layer having controlled release properties may be applied. Furthermore, the coating materials may be biodegradable, biocompatible, biostable, or some combination thereof.

In certain embodiments, the devices coated by the embodiments of the method described herein may comprise tubular medical devices that preferably include a plurality of holes or cells between the abluminal surface and the luminal surface. While the method described herein generally relates to coating tubular devices, the method is more general and may be used to coat non-tubular devices as well. The medical device may comprise a plurality of apertures or open spaces between metallic filaments, segments or regions. Typical structures include: an open-mesh network comprising one or more knitted, woven, or braided metallic filaments; an interconnected network of articulable segments; a coiled or helical structure comprising one or more metallic filaments; and, a patterned tubular metallic sheet. Alternatively, the device may comprise a non-metallic material. Examples of intraluminal stents include endovascular, biliary, tracheal, gastronintestinal, urethral, ureteral, esophageal and coronary vascular stents. The intraluminal stents of the present invention may be, for example, balloon-expandable or self-expandable. A vascular stent may include a plurality of interconnected struts and bends in a plurality of longitudinally connected sinusoidal hoop members. The tubular medical device may be radially expandable from a compressed configuration to a radially expanded configuration. Desirably, the stent is a vascular stent such as the commercially available ZILVER device from Cook Incorporated (Bloomington, Ind.).

Coating Methods

The coating of the device will now be described using three illustrative methods: spray coating, ultrasonic spray deposition, and electrostatic spray deposition. However, it will be understood, that the medical device may be coated using any known manner.

Spray Coating

In one embodiment, the coating material is dissolved in a solvent(s) and sprayed onto the medical device under a fume hood using a spray gun, such as the Model Number 200 spray gun manufactured by Badger Air-Brush Company, Franklin Park, Ill. 60131. Alignment of the spray gun and medical device may be achieved with the use of laser beams, which may be used as a guide when passing the spray gun up and down the medical device being coated.

Ultrasonic Spray Deposition

In another embodiment, the medical device is coated using an ultrasonic spray deposition (USD) process. Ultrasonic nozzles employ high frequency sound waves generated by piezoelectric transducers which convert electrical energy into mechanical energy. The transducers receive a high frequency electrical input and convert this into vibratory motion at the same frequency. This motion is amplified to increase the vibration amplitude at an atomizing surface.

The ultrasonic nozzle is configured such that excitation of the piezoelectric crystals creates a longitudinal standing wave along the length of the nozzle. The ultrasonic energy originating from the transducers undergoes a step transition and amplification as the standing wave traverses the length of the nozzle. The nozzle is designed such that a nodal plane is located between the transducers. For ultrasonic energy to be effective for atomization, the nozzle tip must be located at an anti-node, where the vibration amplitude is greatest. To accomplish this, the nozzle's length must be a multiple of a half-wavelength. In general, high frequency nozzles are smaller, create smaller drops, and consequently have smaller maximum flow capacity than nozzles that operate at lower frequencies.

Liquid introduced onto the atomizing surface absorbs some of the vibrational energy, setting up wave motion in the liquid on the surface. For the liquid to atomize, the vibrational amplitude of the atomizing surface must be carefully controlled. Below a critical amplitude, the energy is insufficient to produce atomized drops. If the amplitude is excessively high, cavitation occurs. Only within a narrow band of input power is the amplitude ideal for producing the nozzle's characteristic fine, low velocity mist. Since the atomization mechanism relies only on liquid being introduced onto the atomizing surface, the rate at which liquid is atomized depends solely on the rate at which it is delivered to the surface.

For example, the medical device is coated using an ultrasonic spray nozzle, such as those available from Sono-Tek Corp., Milton, N.Y. 12547. The solution is loaded into a 10.0 mL syringe, which is mounted onto a syringe pump and connected to a tube that carries the solution to the ultrasonic nozzle. The syringe pump is then used to purge the air from the solution line and prime the line and spay nozzle with the solution. In one embodiment, the stent, solid carbon dioxide plug, and mandrel, described in the first embodiment above, are loaded into the ultrasonic coating chamber for coating application.

Electrostatic Spray Deposition

In another embodiment, the coating material is dissolved in a solvent and then sprayed onto the medical device using an electrostatic spray deposition (ESD) process. The ESD process generally depends on the principle that a charged particle is attracted towards a grounded target. Without being confined to any theory, the typical ESD process may be described as follows:

The solution that is to be deposited on the target is typically charged to several thousand volts (typically negative) and the target held at ground potential. The charge of the solution is generally great enough to cause the solution to jump across an air gap of several inches before landing on the target. As the solution is in transit towards the target, it fans out in a conical pattern which aids in a more uniform coating. In addition to the conical spray shape, the electrons are further attracted towards the conducting portions of the target, rather than towards the non-conductive base the target is mounted on, leaving the coating mainly on the target only.

In the ESD process, the coating solution is forced through a capillary, which is subjected to an electrical field. The solvent mixture leaves the capillary in the form of a fine spray, the shape of which is determined by the electrical field. The medical device is then coated by placing it in the spray and allowing the solvent to evaporate, leaving the desired coating on the surface of the device.

The ESD method allows for control of the coating composition and surface morphology of the deposited coating. In particular, the morphology of the deposited coating may be controlled by appropriate selection of the ESD parameters, as set forth in International Patent Application Serial Number PCT/NL2002/000459, filed Jul. 11, 2002, and published Jan. 23, 2003 as International Publication Number WO 03/006180 (entitled: Electrostatic Spray Deposition (ESD) of biocompatible coatings on Metallic Substrates), the contents of which are incorporated by reference. For example, a coating having a uniform thickness and grain size, as well as a smooth surface, may be obtained by controlling deposition conditions such as deposition temperature, spraying rate, precursor solution, and bias voltage between the spray nozzle and the medical device being coated. The deposition of porous coatings is also possible with the ESD method.

Coating Configurations

Using the method disclosed herein, devices can be coated with one or more therapeutic agents. Preferably, the therapeutic agent is releasably associated with the device, meaning that the therapeutic agent is released from the device following implantation in the body of a patient. Preferably, the therapeutic agent is released in a controlled manner. The therapeutic agent can be incorporated within the material of and/or coated onto the surface.

Selection of the type of therapeutic agent, the portions of the device containing the therapeutic agent and the manner of attaching the therapeutic agent to the device can be chosen to perform a desired therapeutic function upon implantation and, in particular, to achieve controlled release of the therapeutic agent at a desired rate.

A therapeutic agent can be coated directly on a device surface as a separate layer. The therapeutic agent can be bonded to the surface directly via a covalent bond or via a linker molecule which covalently links the therapeutic agent and the surface. The therapeutic agent can also be bound to the surface by ionic, hydrophobic or hydrogen bonding interactions.

Alternatively, a therapeutic agent can be attached to a device surface within a layer including a carrier material. For example, a therapeutic agent can be mixed with the carrier material, such as a polymer, and applied to a surface of the device, for example, by spray or dip coating onto the surface. If the carrier material is biostable, the therapeutic agent can be released by diffusion through the carrier material. If the carrier material is biodegradable, the therapeutic agent can be released upon erosion of the biodegradable carrier material.

The carrier material may include a biostable polymer, a biodegradable polymer or any combination thereof. In one embodiment, the therapeutic agent is blended with a biostable polymer to deposit the therapeutic agent within the porous channels within the biostable polymer that permits release of the therapeutic agent from the device upon implantation. Alternatively, a blend of the therapeutic agent and a bioabsorbable polymer can be incorporated within a biostable polymer matrix to permit dissolution of the bioabsorbable polymer through channels or pores in the biostable polymer matrix upon implantation in the body, accompanied by release of the therapeutic agent.

A layer of porous material can be posited over some, or all, of the therapeutic agent to control the release of the therapeutic agent from the device. Multiple porous layers and/or the pore size in the porous layer can be used to control the rate of release of the therapeutic agent.

Alternatively, in some embodiments the device is at least partially made of porous material. With such embodiments, one or more therapeutic agents may be impregnated into the material of the device. Methods of impregnating therapeutic agents into the structure of non-metallic medical devices are described in U.S. Pat. No. 5,624,704, which is hereby incorporated by reference. One or more therapeutic agents may be impregnated into such devices by contacting the device with the therapeutic agent in a suitable solvent. In some cases, a penetrating ingredient is also added.

Therapeutic Agents

In one embodiment, the therapeutic agent is an antithrombogenic agent. Implantable devices including an antithrombogenic agent are particularly preferred for implantation in areas of the body that contact blood. An antithrombogenic agent is any agent that inhibits or prevents thrombus formation within a body vessel. Types of antithrombotic agents include anticoagulants, antiplatelets, and fibrinolytics. Examples of antithrombotic agents include but are not limited to anticoagulants such as thrombin, Factor Xa, Factor VIIa and tissue factor inhibitors; antiplatelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin.

One example of an antithrombotic agent is a nitric oxide source such as sodium nitroprussiate, nitroglycerin, S-nitroso and N-nitroso compounds. In one embodiment, a material capable of releasing nitric oxide from blood-contacting surfaces can be delivered by the device. Examples of such materials include, but are not limited to, those described in U.S. publication number 2004/0224868A1, published Nov. 11, 2004, and 2002/0115559A1, published Aug. 22, 2002, the contents of which are incorporated by reference.

Other therapeutic agents suitable for inclusion in the devices of the invention include antiproliferative agents, antimitotic agents, antiinflammatory agents, anticancer agents, antimicrobial agents, antibiotics, enzymes, immunosuppressives (such as cyclosporine, tacrolimus (FK-506), sirolimus (rapamycin), rapamycin analogs, tacrolimus, everolimus), mTOR inhibitors, paclitaxel, antiplatelet agents, hormones; anticoagulants, fibrinolytic agents, aspirin, angiogenic agents, anti-sense oligionucleotides, cell cycle inhibitors, inhibitors of matrix metalloproteinases, and combinations thereof. Further examples of therapeutic agents suitable for inclusion in the devices of the present invention are disclosed in U.S. Publication Number 2007/0043431, published Feb. 22, 2007, the contents of which are incorporated by reference.

While the invention has been illustrated and described in detail in the drawings and foregoing description, the same is to be considered as illustrative and not restrictive in character, it being understood that only exemplary embodiments have been shown and described and do not limit the scope of the invention in any manner. The illustrative embodiments are not exclusive of each other or of other embodiments not recited herein. Accordingly, the invention also provides embodiments that comprise combinations of one or more of the illustrative embodiments described above. Modifications and variations of the invention as herein set forth can be made without departing from the spirit and scope thereof, and, therefore, only such limitations should be imposed as are indicated by the appended claims.

I claim:

1. A method of coating a first surface of a device comprising the first surface and a second surface, the method comprising:
    applying a mask to the first surface,
    forming a covering of solid carbon dioxide on the second surface,
    removing the mask from the first surface,
    applying a first coating to the first surface, and
    removing the covering of solid carbon dioxide from the second surface, wherein the covering of solid carbon dioxide is removed subsequent to applying the coating to the first surface.

2. The method of claim 1, wherein the device comprises a stent.

3. The method of claim 2, wherein the first surface is an abluminal surface of the stent.

4. The method of claim 2, wherein the first surface is a luminal surface of the stent.

5. The method of claim 1, wherein the method further comprises applying a second coating over the first coating.

6. The method of claim 1, wherein the method further comprises applying a second coating to the device, the device comprising a porous material.

7. The method of claim 1, wherein the first coating comprises a therapeutic agent.

8. The method of claim 7, wherein the first coating further comprises a polymeric material.

9. The method of claim 7, wherein the first coating further comprises a biodegradable material.

10. The method of claim 7, wherein the therapeutic agent comprises an immunosuppressive agent.

11. The method of claim 7, wherein the therapeutic agent comprises paclitaxel.

12. The method of claim 7, wherein the therapeutic agent comprises an mTOR inhibitor.

13. The method of claim 1, wherein the method further comprises applying a second coating over the first coating, and wherein the second coating comprises a porous material.

14. The method of claim 1, wherein the first coating is applied by a spray method.

15. The method of claim 1, wherein the first coating is applied by ultrasonic spray deposition.

16. The method of claim 1, wherein the method further comprises keeping the device and solid carbon dioxide below a sublimation temperature of the solid carbon dioxide during the application of the coating.

17. The method of claim 1, wherein the method further comprises placing the device and the solid carbon dioxide in a vacuum chamber at a reduced pressure before removing the solid carbon dioxide.

18. The method of claim 1, wherein the mask comprises an elastomeric material.

19. A method of coating a luminal surface of a stent comprising an abluminal surface and a luminal surface, the method comprising:
    placing the stent onto a mandrel to mask the luminal surface of the stent;
    placing a portion of the mandrel attached to the stent into a cavity of a masking body;
    forming a plug of solid carbon dioxide on the abluminal surface;
    removing the mandrel from the stent and plug of solid carbon dioxide; and
    applying a coating to the luminal surface of the stent.

20. A method of coating an abluminal surface of a stent comprising the abluminal surface and a luminal surface, the method comprising:
    placing the stent into a cavity formed in a masking body, wherein the cavity masks the abluminal surface and the masking body comprises an elastomeric material;
    placing a mandrel in the center of the cavity and the stent so that the cavity, stent, and mandrel are approximately concentrically spaced;
    forming a plug of solid carbon dioxide in the cavity of the masking body so that the plug covers the luminal surface of the stent;
    removing the stent and the plug of solid carbon dioxide from the cavity in the masking body;
    applying a coating to the abluminal surface of the stent; and
    warming the stent and the solid plug of carbon dioxide to cause the solid carbon dioxide to sublimate.

* * * * *